(12) United States Patent
Kemperman et al.

(10) Patent No.: US 7,750,167 B2
(45) Date of Patent: Jul. 6, 2010

(54) PROCESS FOR THE PREPARATION OF ASENAPINE AND INTERMEDIATE PRODUCTS USED IN SAID PROCESS

(75) Inventors: Gerardus Johannes Kemperman, Oss (NL); Timothy Lee Stuk, Mattawan, MI (US); Jacobus Johannes Maria Van Der Linden, Oss (NL)

(73) Assignee: N.V. Organon, Oss (NL)

( * ) Notice: Subject to any disclaimer, the term of this patent is extended or adjusted under 35 U.S.C. 154(b) by 540 days.

(21) Appl. No.: 11/773,084

(22) Filed: Jul. 3, 2007

(65) Prior Publication Data

US 2008/0009619 A1 Jan. 10, 2008

Related U.S. Application Data

(60) Provisional application No. 60/806,583, filed on Jul. 5, 2006.

(51) Int. Cl.
*C07D 491/02* (2006.01)
(52) U.S. Cl. .................. 548/421; 548/416; 548/420
(58) Field of Classification Search ............... 548/416, 548/420, 421
See application file for complete search history.

(56) References Cited

U.S. PATENT DOCUMENTS 4,145,434 A   3/1979   Van der Burg

FOREIGN PATENT DOCUMENTS

| WO | WO 95/23600 | 9/1995 |
|----|-------------|--------|
| WO | WO 99/32108 | 7/1999 |

OTHER PUBLICATIONS

Dunne et al., "Co-operative *ortho*-effects on the Wittig reaction. Interpretation of stereoselectivity in the reaction of *ortho*-halo-substituted benzaldehydes and benzylidenetriphenylphosphoranes," *Tet. Lett.* 43, (2002) 2449-2453.
Buck et al., "Ullmann Diaryl Ether Synthesis: Rate Acceleration by 2,2,6,6-Tetramethylheptane-3,5-dione," *Organic Letters* 4 (2002) 1623-1626.
Davidsen et al., "Geminal Acylation-Alkylation at a Carbonyl Center Using Diethyl *N*-Benzylideneaminomethylphosphonate: 2-Methyl-2-Phenyl-4-Pentenal," *Organic Syntheses Coll.* vol. 8 (1993) 451-460.
De Boer et al., "Org-5222: Antipsychotic Dopamine $D_2$ Receptor Antagonist 5-$HT_2$ Receptor Antagonist," *Drugs of the Future* 18 (1993) 1117-1123.
Funke et al., "Physico-chemical Properties and Stability of trans-5-Chloro-2-methyl-2,3,3a,12b-tetrahydro-1H-dibenz[2,3:6,7]oxepino[4,5-c]pyrrolidine Maleate," *Arzneim.-Forsch/Drug.Res 40* (1990) 536-539.
Hosomi et al., "N-(trimethylsilylmethyl)aminomethyl Esthers as Azomethine Ylide Synthons. A New and Convenient Access to Pyrrolidine Derivatives," *Chem. Lett.* (1984) 1117-1120.
Kawasaki et al., "Reverse Aromatic Cope Rearrangement of 2-Allyl-3-alkylideneindolines Driven by Olefination of 2-Allylindolin-3-ones: Synthesis of α-Allyl-3-indole Acetate Derivatives," *J. Org. Chem.* 66 (2001) 1200-1204.
Ma et al., "*N,N*-Dimethyl Glycine-Promoted Ullmann Coupling Reaction of Phenols and Aryl Halides," *Organic Letters* 5 (2003) 3799-3802.
Sawyer, J.S., "Recent Advances in Diaryl Ether Synthesis," *Tetrahedron 56* (2000) 5045-5065.
Vader et al., "The Syntheses of Radiolabelled Org 5222 and its Main Metabolite Org 30526," *J. Labelled Comp. Radiopharm.* 34 (1994) 845-869.

*Primary Examiner*—Golam M Shameem
(74) *Attorney, Agent, or Firm*—H. Eric Fischer; Gerard M. Devlin

(57) ABSTRACT

The invention relates to a novel process for the preparation of asenapine, i.e. trans-5-chloro-2-methyl-2,3,3a,12b-tetrahydro-1H-dibenz[2,3:6,7]oxepino[4,5-c]pyrrole, as well as to novel intermediate products for use in said process.

7 Claims, No Drawings

PROCESS FOR THE PREPARATION OF ASENAPINE AND INTERMEDIATE PRODUCTS USED IN SAID PROCESS

This present invention relates to a novel process for the preparation of trans-5-chloro-2-methyl-2,3,3a,12b-tetrahydro-1H-dibenz[2,3:6,7]oxepino[4,5-c]pyrrole, as well as to novel intermediate products for use in said process.

Trans-5-chloro-2-methyl-2,3,3a,12b-tetrahydro-1H-dibenz[2,3:6,7]oxepino[4,5-c]-pyrrole, which is commonly known as asenapine, is a compound having CNS-depressant activity and having antihistamine and antiserotonin activities (U.S. Pat. No. 4,145,434 to van den Burg). The pharmacological profile of asenapine, its kinetics and metabolism, and the first safety and efficacy studies in human volunteers and in schizophrenic patients have been reviewed (De Boer et al., *Drugs of the Future*, 18(12), 1117-1123, 1993). It has been established that the maleate salt of asenapine, known as Org 5222, is a broad-spectrum, high potency serotonin, noradrenaline and dopamine antagonist.

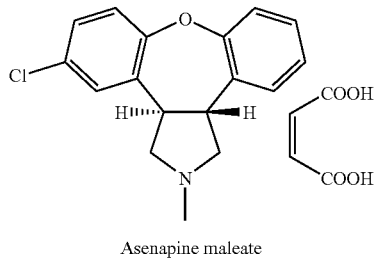

Asenapine maleate

Asenapine exhibits potential antipsychotic activity and may be useful in the treatment of depression (see international patent application WO 99/32108). A pharmaceutical preparation suitable for sublingual or buccal administration of asenapine maleate has been described in the international patent application WO 95/23600 (Akzo Nobel N.V.). Asenapine maleate is now the subject of clinical studies, making large scale synthesis of the drug substance necessary.

A general methodology for the preparation of asenapine is disclosed in U.S. Pat. No. 4,145,434. Physical-chemical properties of the drug substance Org 5222 have been reported (Funke et al. *Arzneim.-Forsch/Drug.Res.* 40, 536-539, 1990). Additional synthetic methods for the preparation of Org 5222 and radiolabelled derivatives thereof have also been described (Vader et al., *J. Labelled Comp. Radiopharm.* 34, 845-869, 1994).

There is a need for synthetic procedures for the preparation of asenapine which can reliably be carried out on an industrial scale.

The present invention provides a process for the preparation of trans-5-chloro-2-methyl-2,3,3a,12b-tetrahydro-1H-dibenz[2,3:6,7]oxepino[4,5-c]pyrrole (Formula I)

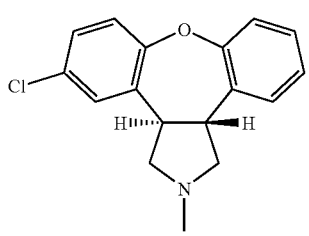

characterised in that an E-stilbene derivative of Formula II

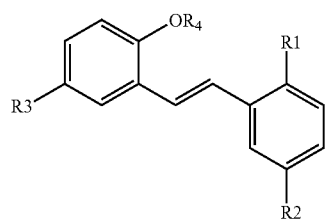

is reacted with an azomethine ylide to provide a trans-pyrrolidine derivative of Formula III,

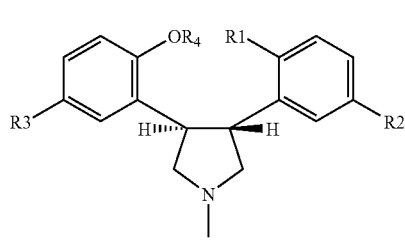

In Formula II and Formula III, $R_1$ is F, Br or I;

$R_2$ and $R_3$ are different and each is selected from H and Cl; and $R_4$ is H or a hydroxyl protecting group. Subsequent removal of the protecting group, when present, and treatment under conditions which effect an intramolecular ring closure yield the compound of Formula I.

In the definition of Formula II, $R_4$ can be a hydroxy protecting group which is stable under the reaction conditions leading to the trans-pyrrolidine derivative of Formula III. Examples of such protecting groups are the tetrahydropyranyl group, a silyl protecting group or an acyl group. Further examples are known in the art. See, for example, Wuts, P. G. M. and Greene, T. W.: *Protective Groups in Organic Synthesis*, Third Edition, Wiley, New York, 1999. A preferred protecting group is the acyl group, especially the acetyl group.

Throughout this disclosure, compounds represented by structural formulae having a pair of bold and hashed wedged bonds, as shown, e.g., in the formula of compounds (I) and (III), refer to the "trans" diastereoisomer. Each of the compounds may exist as a single enantiomer having the absolute stereochemical configuration indicated by the wedged bonds, or having the opposite absolute configuration, or as a mixture of enantiomers (e.g., racemate) having the relative stereochemical configuration indicated by the wedged bonds.

In a first reaction step of the process of the invention, an E-stilbene derivative of Formula II is reacted in a [3+2] dipolar cycloaddition reaction with an in situ generated azomethine ylide to provide a trans-pyrrolidine derivative of Formula III. It is thought that the reaction proceeds in a concerted manner in which all bonds are created simultaneously. Consequently, the stereochemistry is conserved in the product. When the reaction is started with an E-stilbene derivative, the trans pyrrolidine ring is formed exclusively. The stereoselectivity of the dipolar addition step in the process of the invention represents a large advantage with respect to the good overall yield of the process.

The required azomethine ylide, which may be represented by the following dipolar structure

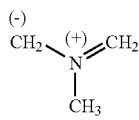

can be generated, for example, in situ from trimethylamine-N-oxide dihydrate (TMNO.2H$_2$O) or trimethylamine-N-oxide anhydrate (TMNO) with lithium di-isopropylamide (LDA) or lithium tetramethylpiperidide. The dipolar addition reaction can be carried out by addition of LDA to a mixture of an E-stilbene of Formula II and TMNO in an aprotic solvent, such as tetrahydrofuran. Preferably, LDA is added slowly to control the reaction temperature, preferably below 30° C., and to effect the dissolution of the trimethylamine-N-oxide.

When R$_1$ is Br or I in Formula II, the dipolar addition using TMNO produced the pyrrolidine of Formula III in a good yield and purity, and it proved possible to crystallise the resulting pyrrolidine derivatives of Formula III directly from an n-pentane/ethyl acetate mixture or an ethanol/water mixture.

In a preferred process, the required azomethine ylide is generated in situ from N-methoxymethyl-N-trimethylsilylmethyl-N-methylamine (Formula 3, below) via activation with trifluoroacetic acid or cesium fluoride (Hosomi, A. et al. *Chem. Lett.* 1117-1120, 1984).

The novel aminomethyl ether (3) can be prepared from the alkylation of methylamine by (chloromethyl)trimethylsilane (1) to yield the secondary amine (2) which can be subsequently treated with formaldehyde in methanol solution:

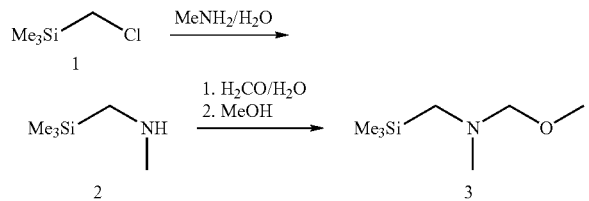

The use of reagent (3) offers many advantages. For example, the process of the invention can be carried out with higher throughputs because the aminomethyl ether reagent allows the use of smaller volumes of solvent. Furthermore, the use of reagent (3) provides for a safer method of synthesis because the process of generating the azomethine ylide is much less exothermic as compared to the process using trimethylamine-N-oxide. In addition, reagent (3) does not react to any appreciable extent with the Z-stilbene derivative so that the synthesis may tolerate more of the Z-isomer.

In a preferred embodiment, the dipolar addition reaction is carried out using stilbene derivatives of Formula II wherein R$_4$ represents a protecting group. The protecting group, such as an acetyl group, deactivates the hydroxy-phenyl group for electrophilic aromatic substitution reactions that may compete with the dipolar addition reaction leading to the pyrrolidine of formula II. As a result the occurrence of side products can be minimised.

In the second step of the process, a trans-pyrrolidine derivative of Formula IIIA,

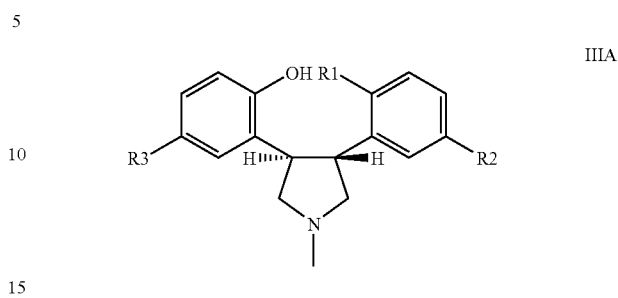

is treated under conditions which effect an intramolecular ring closure reaction to produce trans-5-chloro-2-methyl-2,3,3a,12b-tetrahydro-1H-dibenz[2,3:6,7]oxepino-[4,5-c]pyrrole (asenapine, Formula I).

The intramolecular ring closure reaction to form the 7-membered oxepine ring of asenapine can be performed with an Ullmann-type reaction, i.e. treatment of a compound of Formula IIIA in a solvent with copper(0) powder, with a copper(I) salt or with a copper (II) salt in the presence of a base at elevated temperatures (Ma, D., Cai, Q., *Organic Letters*, 5, 3799-3802, 2003; Buck, E., et. al, *Organic Letters* 4, 1623-1626, 202; Sawyer, J. S., *Tetrahedron* 5045-5065, 2002). An additive, such as N,N-dimethylglycine, N-methylglycine, 2,2,4,4-tetramethyl-3,5-heptanedione (TMHD) or 8-hydroxyquinoline, may be used to increase the solubility of the copper ions. Suitable bases include Cs$_2$CO$_3$, K$_2$CO$_3$, pyridine, NaOH, KOH or CsF. Useful copper sources include Cu-powder, CuI, CuBr, CuCl, Cu(CO)$_3$ (copper(II)carbonate, Cu(OAc)$_2$ (copper(II)acetate), Cu(OTf)$_2$ (copper(II)trifluoromethanesulfonate), Cu$_2$O or CuSO$_4$.

Suitable conditions for complete conversion of a compound of Formula IIIA to asenapine are the use of CuCl (0.25 eq.), N,N-dimethylglycine (0.25 eq.) and Cs$_2$CO$_3$ (1.1 eq. ) in refluxing dioxane for about 24 hours. Solvents for use in the Ullman cyclisation reaction on an industrial scale at temperatures between about 80-110° C. are dimethylformamide (DMF), dimethylacetamide (DMA), N-methylpyrrolidone (NMP), pyridine, dioxane, toluene, xylene, diethyleneglycoldimethylether (Diglyme), 2-methyltetrahydrofuran, and the like.

Preferred reaction conditions for the Ullman cyclisation reaction at industrial scale are the use of dimethylacetamide or mixtures thereof with toluene as the solvent system, the use of Cs$_2$CO$_3$, NaOH, KOH or K$_2$CO$_3$ as the base, and the use of dimethylglycine in combination with copper(I)chloride as the catalyst.

A particularly useful embodiment of the invention is the process for the preparation of asenapine of Formula I,

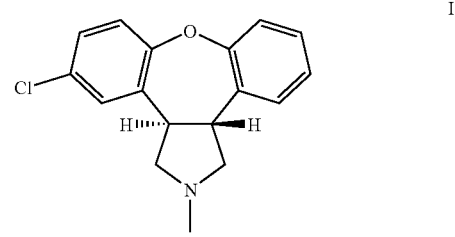

or a salt thereof, in which (E)-2-(2-bromostyryl)-4-chlorophenyl acetate,

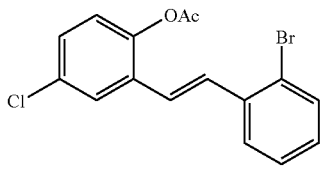

is reacted in an inert solvent, such as toluene, with the azomethine ylide generated in situ from N-methoxymethyl-N-trimethylsilylmethyl-N-methylamine with the aid of trifluoroacetic acid to provide trans-N-methyl-4-(2-bromophenyl)-3-(2-acetoxy-5-chlorophenyl)-pyrrolidine,

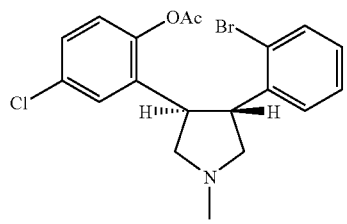

The pyrrolidine derivative is treated under basic conditions, such as aqueous alkali solution, to remove the acetyl group. Subsequent treatment of the deprotected pyrrolidine derivative under Ullmann conditions with the aid of a copper (I) salt to effect the intramolecular ring closure gives asenapine, which may be optionally converted to a pharmaceutically acceptable salt.

Another aspect of the invention provides the novel trans-pyrrolidine derivative of Formula III,

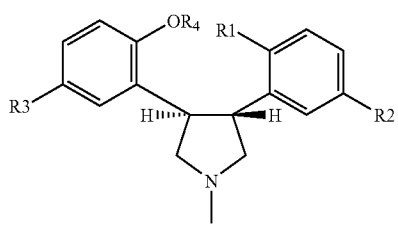

wherein $R_1$ is F, Br or I; $R_2$ and $R_3$ are different and are each selected from H and Cl; and wherein $R_4$ is H or a hydroxyl protecting group, as previously defined, or a salt thereof.

Still another aspect the present invention provides the novel E-stilbene-derivative of Formula II

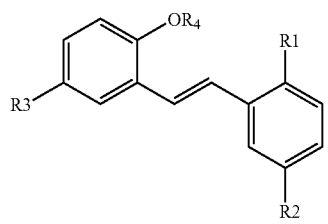

wherein $R_1$ is F, Br or I; $R_2$ and $R_3$ are different and are each selected from H and Cl; and wherein $R_4$ is H or a hydroxyl protecting group, as previously defined. These stilbene derivatives are useful intermediates in industrially producing the pharmaceutically active compound of Formula I, i.e. asenapine.

The E-stilbene derivatives of Formula II can for instance be prepared using a Wittig reaction in which a triphenylphosphonium halogenide of Formula IV, below, is reacted with an appropriate salicylic aldehyde of Formula VI in refluxing solvents such as chloroform, tetrahydrofuran or mixtures thereof with ethanol, in the presence of an equivalent amount of a base, such as diisopropylethylamine, DBU, DABCO, potassium tert-butoxide or sodium ethoxide, wherein $R_1$, $R_2$ and $R_3$ are each as defined above for Formula II and III. The Wittig reaction typically results in a mixture of E- and Z-isomers, the best ratio's being approximately 70:30. The pure E-isomer (Formula II) may be isolated via chromatography.

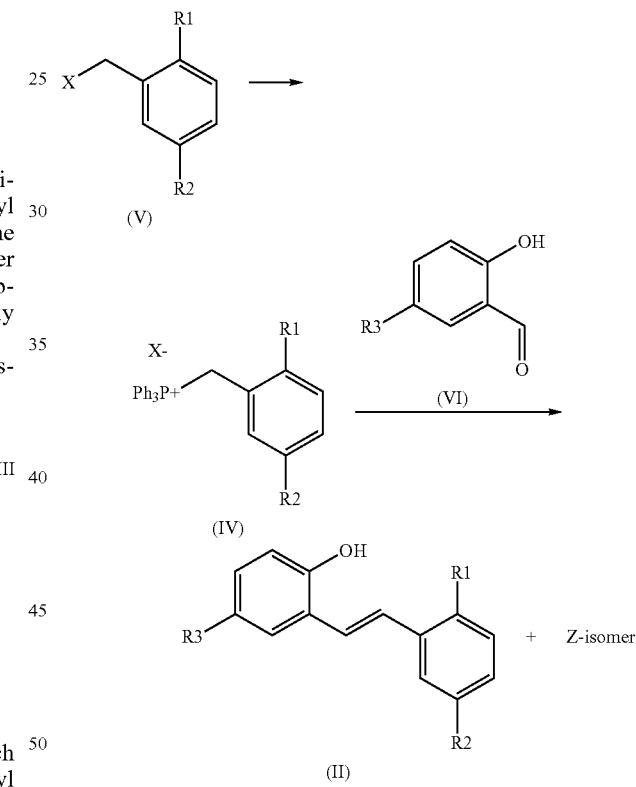

The triphenylphosphonium halogenide of Formula IV can be prepared by treatment of a compound of Formula V, wherein $R_1$ is F, Br or I, and $R_2$ is H or Cl, and wherein X represents halogen, preferably Cl of Br, with triphenylphosphine in refluxing toluene solution.

A preferred method of synthesizing E-stilbene derivatives of Formula II uses a phosphonate ester derivative having Formula VII, below. The phosphonate ester derivative can be prepared by heating a compound of Formula V, either neat or using a solvent such as toluene, with an equimolar amount of triethylphosphite (Davidsen, S. K.; Phllips, G. W.; Martin, S. F. *Organic Syntheses*, Coll. Vol. 8, p. 451 (1993); Vol. 65, p. 119).

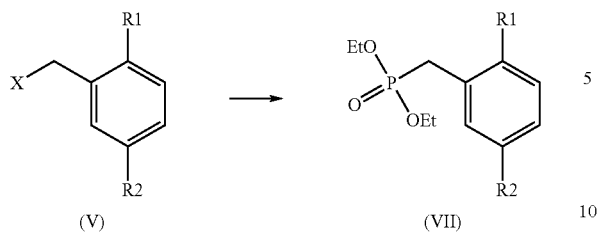

In a subsequent Wittig-Horner reaction (T. Kawasaki, et al., *J. Org. Chem.*, 66, 1200-1204, 2001; *Tet. Lett.* 43, 2449, 2001) the phosphonate ester of Formula VII is treated in a solvent, such as tetrahydrofuran, with a base, such as potassium tert-butoxide, butyllithium, sodiumhydride or sodiummethoxide, to produce an intermediate stabilized phosphonate anion which reacts with a salicylaldehyde derivative of Formula VI to selectively yield an E-stilbene of Formula II.

Suitable salts of asenapine of Formula I and of the trans-pyrrolidine derivatives of Formula III include the salts obtained from the combination with an organic base, such as trimethylamine, triethylamine and the like. Suitable acid addition salts can be obtained from the treatment with a mineral acid such as hydrochloric acid, hydrobromic acid, phosphoric acid and sulfuric acid, or with an organic acid such as, for example, ascorbic acid, citric acid, tartaric acid, lactic acid, maleic acid, malonic acid, fumaric acid, glycolic acid, succinic acid, propionic acid, acetic acid and methane sulfonic acid. The preferred acid addition salt of asenapine of Formula I is the maleate salt, i.e. Org 5222.

The invention is illustrated by the following Examples.

EXAMPLES

The following examples are illustrative and non-limiting and represent specific embodiments of the present invention. In each of the examples below, the compound asenapine (Formula I), and its precursor the trans-pyrrolidine derivative of Formula III, are racemates, and the pairs of bold wedged bonds or bold and hashed wedged bonds used in their structural formulae indicate relative stereochemical configuration.

General Methods:

NMR spectra were recorded on a Bruker DPX 400. Chemical shifts are reported in parts per million (ppm). $^1$H-NMR chemical shifts are referenced to TMS as internal standard (abbreviation s singlet; d doublet; t triplet, dd double doublet, m multiplet). Mass spectra were recorded on a PE SCIEX API 165. GC chromatograms were obtained using an Agilent HP6890N gas chromatograph outfitted with a Restek RTX-column. HPLC chromatograms were obtained using an Agilent HP1100 liquid chromatograph.

Example 1

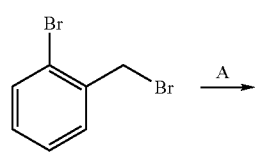

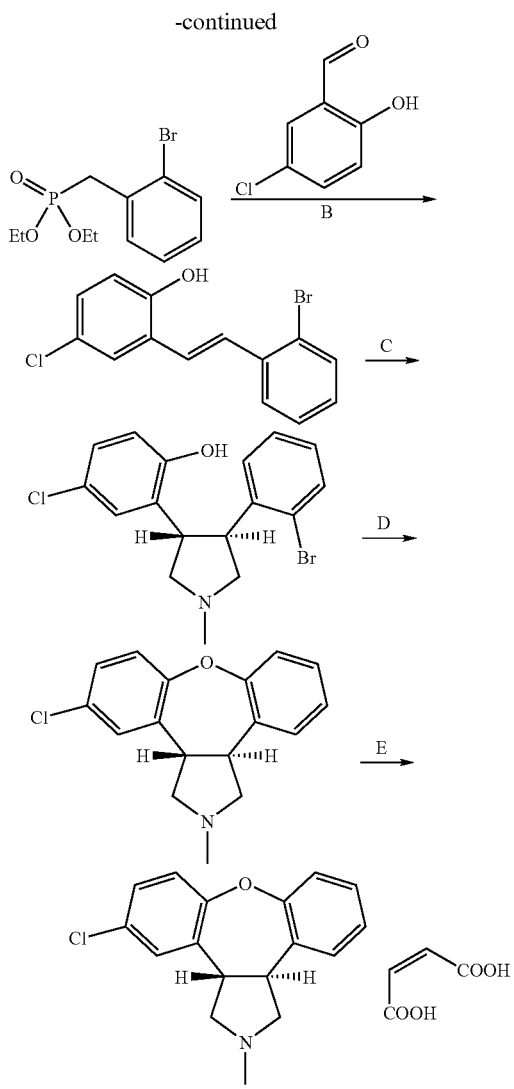

A: (2-Bromo-benzyl)-phosphonic acid diethyl ester

2-Bromobenzyl bromide (1048 g, 4.2 mol) was melted in a water bath of 60° C. and dissolved in xyleen (734 ml). The solution was heated to 80° C. Next triethyl phosphite (766 ml, 4.46 mol) was added in three equal portions to the reaction mixture in 60 minutes. The mixture was stirred overnight at 110° C. The reaction mixture was co-evaporated twice with 400 ml of xylene. The xylene was removed in vacuo at 60° C. The product was dried in a vacuum oven at 60° C. and was used without further purification.

$^1$H-NMR: (CDCl$_3$): 1.33 (6H, t, 2×CH$_3$); 3.43 (1H,s,CH$_2$-a); 3.54 (1H,s,CH$_2$-b); 4.12 (4H, q, 2×CH$_2$O); 7.17 (1H, m, ArH); 7.34 (1H, m, ArH); 7.55 (1H, m, ArH), 7.62 (1H, m, ArH)

$^{31}$P-NMR: (CDCl$_3$): 23.81

Mass analysis: M+1=307 and 309 (Br-isotopes) found

B: trans-2-bromo-5'-chloro-2'-hydroxystilbene

5-Chlorosalicylaldehyde (188 g, 1.2 mol) was added to a solution of (2-bromo-benzyl)-phosphonic acid diethyl ester (369 g, 1.2 mol) in tetrahydrofuran (1500 ml) under nitrogen.

A solution of potassium tert-butoxide (300 g, 2.68 mol) in tetrahydrofuran (3000 ml) was added while keeping the temperature at 33° C. After completion of the reaction water (1800 ml) was added followed by 4N HCl (450 ml). The organic layer was washed with sodium carbonate solution (500 ml) and saturated NaCl solution. The organic layer was evaporated under reduced pressure at 50° C. to give trans-2-bromo-5'-chloro-2'-hydroxystilbene (301.9 g, 92%).

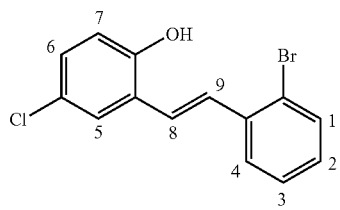

$^1$H-NMR (CDCl$_3$): 6.70 (1H, d, H-7); 7.12 (1H, d, H-6); 7,15 (1H, t, H-2 or H-3); 7.21 (1H, d H-9); 7.35 (1H, t, H-2 or H-3); 7.46 (1H, d, H-8,); 7.52 (1H, d, H-5); 7.58 and 7.68 (2×2H, 2×d, H-1 and H-4)

C: trans-N-methyl-2-(2-bromophenyl)-3-(2-hydroxy-5-chlorophenyl)-pyrrolidine

To a solution of trans-2-bromo-5'-chloro-2'-hydroxystilbene (81 g, 261 mmol) in tetrahydrofuran (570 ml) trimethylamine-N-oxide.dihydrate (43.4 g, 390 mmol) was added at ambient temperature. Lithium diisopropylamide in heptane/THF (2M, 1070 ml, 2140 mmol) was then added during the course of 1 hour while maintaining the temperature below 40° C. After completion of the reaction water (120 ml) was added. Solvent was evaporated to a small volume after which ethyl acetate (250 ml) was added. The pH was adjusted to pH 8 with 18 % hydrochloric acid (~250 ml) and ethyl acetate (250 ml) was added. The organic layer was separated and the aqueous layer was again extracted with ethyl acetate (2×120 ml). The combined organic layers were washed with water (325 ml) and with brine, dried (MgSO$_4$) and then evaporated in vacuo. The resulting oil was crystallised from ethanol/water (1/1, v/v) to give the title pyrrolidine (62.0 g, 79%). Purity according to HPLC is 99% a/a.

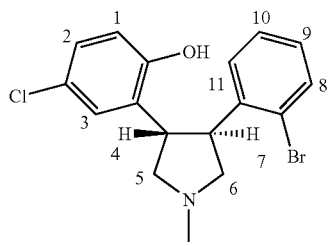

$^1$H-NMR (MeOD): 2.50 (3H, s, CH$_3$), 2.52+3.09+3.10+3.45 (4×1H, t, dd, t, t, Ha-5, Hb-5, Ha-6, Hb-6), 3.62+4.14 (2×1H, 2 xm, H4+H7), 6.72 (1H, d, H-1), 6.94 (1H, d, H-3), 6.98 (1H, d, H-2), 7.10+7.35 (2×1H, 2×t, H-10+H-9), 7.52+7.58 (2×1H, 2×d, H-8+H-11).

D+E: Asenapine maleate; Org 5222

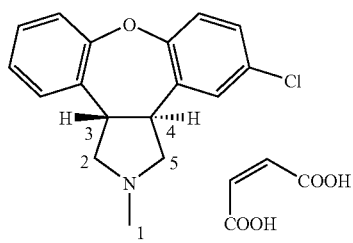

Process 1:

To a mixture of trans-N-methyl-2-(2-bromophenyl)-3-(2-hydroxy-5-chlorophenyl)-pyrrolidine (103 g; 280.8 mmol) and dioxane (520 ml) were added under a nitrogen atmosphere cesium carbonate (109.79 g; 1.2 eq), N,N dimethylglycine (7.2 gram; 0.25 eq) and copper iodide (13.36 g; 0.25 eq). The mixture was heated to reflux, stirred for 68 hours at reflux temperature and then filtered over dicalite. The dicalite was washed with dioxane (3×50 ml). The dioxane was evaporated, whereupon the residue was dissolved in ethanol (1000 ml). Under stirring aqueous hydrobromic acid (48%; 31.5 ml) was added to the ethanol solution. The suspension was stirred for 16 hours. The crystalline asenapine hydrobromide salt was collected and dried under vacuum. The product was stirred in water (500 ml) whereupon the pH was adjusted to 8 by the addition of aqueous sodium hydroxide (2N). The water layer was extracted with dichloromethane. The organic layer was washed with water (200 ml), dried on magnesium sulphate and evaporated. The residue was dissolved in ethanol (50 ml). To this solution was added a solution of maleic acid (16.6 gram; 142.6 mmol) in ethanol (20 ml) and water (6 ml). The mixture was stirred overnight. Ethanol (20 ml) was added to the thick mass and the suspension was stirred for another hour. The asenapine maleate was collected and dried under vacuum at 40° C. yielding 44 g (39%). Purity according to HPLC is 99.8% a/a.

$^1$H-NMR (CDCl$_3$): 2.58 (3H, s, 1-N—CH$_3$); 3.14 (2H, m, H-3 and H-4); 3.21 and 3.62 (m, 2×2H, 2×H-2 and 2×H-5); 6,24 (2H, s, vinylic H'2 of maleic acid), 7.01-7.36 (7H, m, aromatic H's).

ESI_MSMS: The observed fragments at m/z 44,166,194, 201, 215, 220, 229 being [C2H6N]+,[C12H6O]+., [C14H10O]+., [C12H6ClO]+, [C13H8ClO]+, [C16H12O]+., [C14H10ClO]

Melting-point: 140° C.

Process 2

Potassium carbonate (6.24 g; 45.0 mmol) and copper-powder (0.96 g; 15.1 mmol) were suspended in dimethylacetamide (25 ml). The temperature was brought to 140° C. and nitrogen was led through the suspension during 30 minutes. trans-N-Methyl-2-(2-bromophenyl)-3-(2-hydroxy-5-chlorophenyl)-pyrrolidine (15 g; 40.9 mmol) was then added and the reaction mixture was stirred for 29 hours. The suspension was filtered over dicalite and the solvent was evaporated. The residue was dissolved in toluene (100 ml) and washed twice with ammonia (50 ml) and with water (50 ml). The toluene layer was dried on magnesium sulphate and evaporated. The residue was dissolved in ethanol (18.2 ml), whereupon a solution of maleic acid (4.83 g; 41.4 mmol) in ethanol (5.2 ml) and water (1.82 ml) was added under stirring. After stirring for 16 hours the crystals of asenapine maleate were collected and dried under vacuum at 40° C. yielding 8.9 g (54%). Purity according to HPLC is 99.9% a/a.

¹H-NMR (CDCl₃): 2.58 (3H, s, 1-N—CH₃); 3.14 (2H, m, H-3 and H-4); 3.21 and 3.62 (m, 2×2H, 2×H-2 and 2×H-5); 6.24 (2H, s, vinylic H'2 of maleic acid), 7.01-7.36 (7H, m, aromatic H's).

ESI_MSMS: The observed fragments at m/z 44,166,194, 201, 215, 220, 229 being [C2H6N]+,[C12H6O]+., [C14H10O]+., [C12H6ClO]+, [C13H8ClO]+, [C16H12O]+., [C14H10ClO].

Melting-point: 140° C.

Process 3

To a solution of trans-N-Methyl-2-(2-bromophenyl)-3-(2-hydroxy-5-chlorophenyl)-pyrrolidine (10 g; 27.3 mmol) in methanol (100 ml) was added KOH (1.68 g, 29.9 mmol). The obtained clear solution was stirred at 40° C. for 15 minutes. The solvent was evaporated, toluene (73 ml) and DMA (18 ml) was added, followed by CuCl (1.00 g, 10 mmol), dimethylglycine (2.20 g, 21.3 mmol) and potassium carbonate (3.77 g, 27.3 mmol). After refluxing for 4 hours, the solvent was removed in vacuo. The reaction mixture was dissolved in toluene (55 ml) and extracted with 5% ammonia solution (3×55 ml). The toluene layer was dried on magnesium sulphate and evaporated. The residue was dissolved in 2-propanol (10 ml), whereupon a solution of maleic acid (3.48 g; 30.0 mmol) in 2-propanol (68 ml) and water (1.82 ml) was added under stirring. After stirring for 16 hours the crystals of asenapine maleate were collected and dried under vacuum at 40° C. yielding 6.0 grams (55%). Purity according to HPLC is 99% a/a.

¹H-NMR (CDCl₃): 2.58 (3H, s, 1-N—CH₃); 3.14 (2H, m, H-3 and H-4); 3.21 and 3.62 (m, 2×2H, 2×H-2 and 2×H-5); 6,24 (2H, s, vinylic H'2 of maleic acid), 7.01-7.36 (7H, m, aromatic H's).

ESI_MSMS: The observed fragments at m/z 44,166,194, 201, 215, 220, 229 being [C2H6N]+,[C12H6O]+., [C14H10O]+., [C12H6ClO]+, [C13H8ClO]+, [C16H12O]+., [C14H10ClO].

Melting-point: 140° C.

Example 2

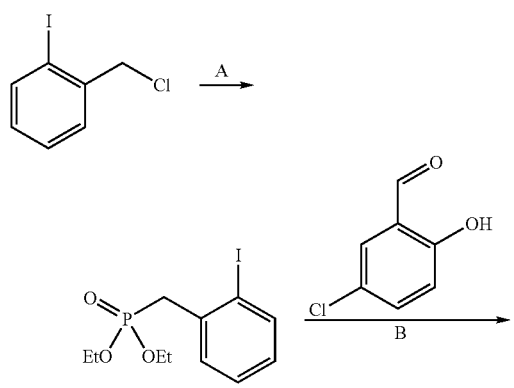

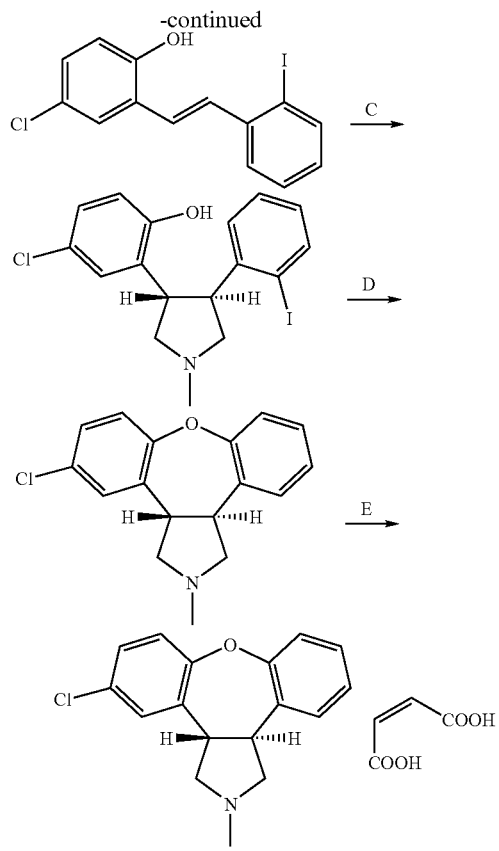

A: (2-Iodo-benzyl)-phosphonic acid diethyl ester

Triethyl phosphite (ca 66.6 ml; 94% pure; ca. 396.8 mmol) and 2-iodobenzyl chloride 1 (100 g, 400 mmol; melted prior to use) were mixed with xylene (65 ml) in a 250 ml round-bottomed flask. The clear solution was heated to reflux while stirring for 24 hours. The reaction was followed by GC and ¹H-NMR (CDCl₃). The disappearing proton resonance of 2H, s, CH₂I at 4.73 ppm and the new 2H, d, CH₂PO(OEt)₂ at 3.47 ppm were indicative for the progress of the reaction.

¹H-NMR (CDCl₃): 1.33 (6H, t, 2×CH₃); 3.47 (2H, d, CH₂PO(OEt)₂); 4.12 (q, 4H, 2×CH₂O); 6.99 (1H, m, ArH); 7.35 (1H, m, ArH); 7.54 (1H, m, ArH), 7.89 (1H, m, ArH).

Mass analysis: M+1=355 (Cl-isotopes found), M−1=355 (Cl-isotopes found),

B: trans-2-Iodo-5'-chloro-2'-hydroxystilbene

The resulting solution of crude (2-iodo-benzyl)-phosphonic acid diethyl ester was cooled to room temperature and then added to a solution of 5-chlorosalicylaldehyde (62.14 g, 396.8 mmol; 1.0 eq.) in THF (1000 ml). The solution was cooled with an ice bath to ca. 0° C. KOtBu (97.2 g, 868 mmol, 2.19 eq.) was added in portions over 5 minutes and an orange, almost clear solution was obtained. Additional THF (100 ml) was added. After stirring for an additional 10 minutes the ice bath was removed and reaction mixture was stirred while warming to room temperature. After 1 hour water (250 ml) was added and a clear orange solution was obtained. Ethyl acetate (400 ml) was added followed by saturated aqueous NaCl (100 ml). The organic phase was separated and concentrated under vacuum to give 155 g (>100%) oil. Then, 2N HCl (aq.; 250 ml) was added followed by ethyl acetate (250 ml). The organic phase was separated, dried with Na₂SO₄, and evaporated under vacuum to give 127 g solid. This solid was then stirred in n-pentane (500 ml) for 15 minutes at room temperature. The beige solid was filtered over a glass filter, washed with n-pentane (50 ml) and dried under vacuum at the rotary evaporator. The yield of the title stilbene was 111 grams (79%). The product was used without further purification.

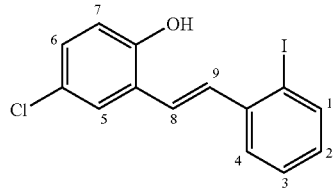

Mass analysis: M+1=356 (Cl-isomer found).

¹H-NMR (CDCl₃): 6.8.1 (1H, d, H-7 ); 7.05 (1H, d, H-6); 7,18 (1H, t, H-2 or H-3); 7.22 (1H, d H-9); 7.34 (1H, t, H-2 or H-3); 7.42 (1H, d, H-8,); 7.60 (1H, d, H-5); 7.52 and 7.98 (2×2H, 2×d, H-1 and H-4)

C: trans-N-methyl-2-(2-iodophenyl)-3-(2-hydroxy-5-chlorophenyl)-pyrrolidine

A mixture of trans-2-iodo-5'-chloro-2'-hydroxystilbene (56.1 grams, 157.6 mmol) and trimethylamine N-oxide dihydrate (52.55 g, 472.8 mmol) was dissolved in THF (570 ml) at room temperature while stirring. Not all of the trimethylamine N-oxide dihydrate dissolved. The mixture was cooled with an ice bath to 0° C. Then, a cooled LDA solution of ca. 4° C. (577.5 ml, 1.8 M in heptane/THF/ethylbenzene; 1.04 moles) was added drop wise with a dropping funnel over 25 minutes. The internal temperature rose to ca. 20-26° C. After the addition was complete the temperature of the resulting orange/yellow solution dropped to ca. 8° C. within 10 minutes. A sample was taken, quenched with some water and analyzed by LC to show >90% cycloadduct The ice-bath was removed and the reaction mixture was stirred for an additional 4 hours while warming to room temperature. Water (140 ml) was added and the mixture was stirred overnight at room temperature. Then 2 N HCl (200 ml) was added followed by ethyl acetate (500 ml). The organic layer was separated. The aqueous layer, which was still slightly basic (pH indicator paper), was again extracted with ethyl acetate (100 ml). The combined organic extracts were dried with Na₂SO₄. Evaporation under vacuum gave an oil. Diethyl ether (100 ml) was added to give a solution. Upon addition of n-pentane (300 ml) to this ether solution while stirring gave a yellow precipitate. Filtration over a glass filter and washing with n-pentane (2×25 ml) gave after drying under vacuum the pure cycloadduct (46.5 g, 112.6 mmol; LC>95% pure) as a yellow solid in 72% yield. M.p.: 123.1° C. (onset), 126.9° C. (peak). The filtrates were combined and evaporated under vacuum to give 23 grams oil, which contained a lot of product according to NMR analysis. Purification by chromatography on silica gel, eluting with ethyl acetate gave a second crop (17 g; 41.1 mmol; 26%). The overall yield was ca. 98%.

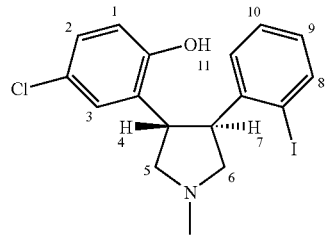

Mass analysis: M+1=414 (Cl-isomer found), M−1=412 (Cl-isomer found),

¹H-NMR (CDCl₃): 2.60 (3H, s, CH₃), 2.30+2.96+3.77+3.42 (4×1 H, t, dd, t, t, Ha-5, Hb-5, Ha-6, Hb-6), 3.22 (2H, m, H4+H7), 6.82 (1H, d, H-1), 6.92 (1H, d, H-3), 7.02 (1H, d, H-2), 7.32+7.15 (2×1H, 2×t, H-10 +H-9), 7.51+7.85 (2×1H, 2×d, H-8+H-11).

D: Asenapine

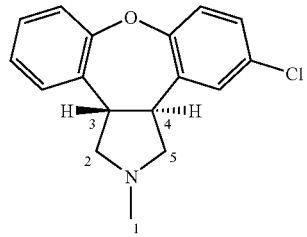

Process 1

A mixture trans-N-methyl-2-(2-iodophenyl)-3-(2-hydroxy-5-chlorophenyl)-pyrrolidine (46.5 g 112.6 mmol) and cesium carbonate (100 grams, 306.9 mmol) in N,N-dimethylacetamide (DMA, 350 ml) was heated to 140° C. (internal temperature) while stirring. After 2 hours no Asenapine was observed by NMR analysis of a small sample; only starting material was present. Then, again cesium carbonate (98 g) was added (in total 607.7 mmol Cs₂CO₃; used) and the mixture was heated overnight (16 hours). According to NMR analysis a mixture of starting material and Asenapine was obtained. The product was subjected to purification by chromatography. ¹H-NMR (CDCl₃) was in full agreement.

Process 2

A mixture of trans-N-methyl-2-(2-bromophenyl)-3-(2-hydroxy-5-chlorophenyl)-pyrrolidine (27 g, 65.4 mmol), cesium carbonate (42.7 g, 131 mmol,) CuI (4.98 g, 26.2 mmol) and TMHD (2.39 g, 13.1 mmol, 20 mol %) in NMP (250 ml) was heated to 160° C. (internal temperature). After 1 hour the reaction was complete. After 4 hours the mixture was then concentrated under vacuum with a Kugelrohr apparatus to remove most of the the NMP. ¹H-NMR (CDCl₃) was in full agreement.

Example 3

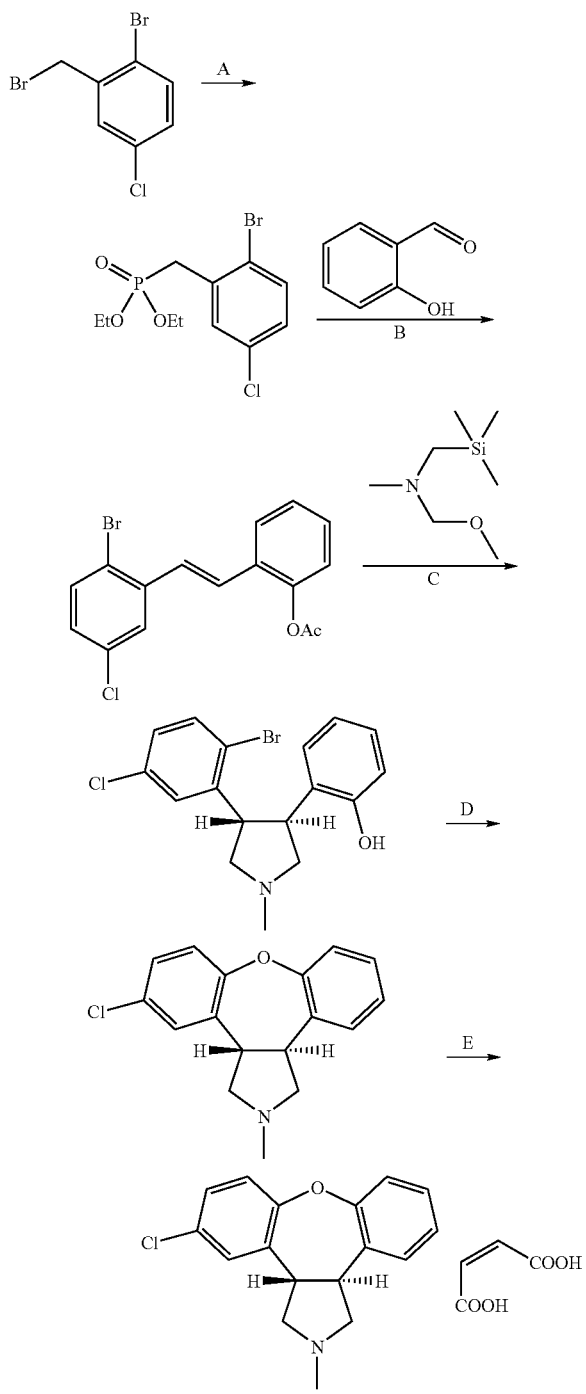

A+B: trans-2-Acetoxy-2'-bromo-5'-chlorostilbene

2-Bromo-5-chloro-benzylbromide (462 g, 1625 mmol) was heated in triethyl phosphite (297 g, 1769 mmol) for 2 hours at 115° C. The mixture was cooled down. To salicylaldehyde (216 g, 1769 mmol) in tetrahydrofuran (4610 ml) at −10° C. was added portionwise KOtBu (495 g, 4411 mmol). The mixture mentioned above was added at −10° C. The reaction mixture was stirred for 2 hours and then acetic anhydride (461 g, 4516 mmol) was added. After 15 minutes of stirring hydrogen chloride (2900 ml 1N, 2900 mmol) was added. The layers were separated and the organic layer was washed with brine (2 L). The organic layer was concentrated under vacuum. The product was crystallized from ethanol (4250 ml) at 20° C. to −10° C. The product was isolated by filtration and dried under vacuum for 24 hours. Yield 514.8 g (90%) of the title stilbene. Purity according to HPLC is >99.5% a/a.

$^1$H-NMR (CDCl$_3$): 2.39 (3H, s, CH$_3$), 7.03 (1H, d, J=16 Hz, olefin H), 7.10 (2H, m, H3+H4), 7.30+7.35 (2×H, t, t, H2+H3), 7.39 (1H, d, J=16 Hz, olefin H), 7.49+7.56+7.68 (3×1H, d, d, d, H4'+H3'+H6')

Melting Point: 134-135° C.:

Mass: M+1=351 and 353 (Br-isotopes) found.

C: trans-N-methyl-2-(2-hydroxyphenyl)-3-(2-bromo-5-chlorophenyl)-pyrrolidine trans-2-Acetoxy-2'-bromo-5'-chlorostilbene (1189 g, 3381 mmol) was dissolved in toluene (5350 ml) and trifluoroacetic acid (10.42 ml, 165 mmol) at 33° C. N-methoxymethyl-N-trimethylsilyl-N-methylamine (670 g, 4153 mmol) was added in the course of 1 hour. The organic layer was concentrated under vacuum to an oil. This oil was dissolved in methanol (4160 ml) at 30° C. Potassium hydroxide (209 g, 3725 mmol) in water (900 ml) was added. After 30 minutes, the pH was adjusted to 8-9 with 3N HCl (approx. 200 ml). The mixture was stirred for 30 minutes and filtered. The product was dried for 24h under vacuum, yielding the title pyrrolidine in 1188 grams (96%). Purity according to HPLC is >99,0% a/a.

$^1$H-NMR: (CDCl$_3$) 2.25 (1H, t, H a), 2.53 (3H, s, CH$_3$), 2.86+3.25+3.31+3.67+4.05 (5×H, t, d, m, t, m, H1b+H4a + H3+H4b +H2), 6.62+6.82+6.92+7.08+7.12+7.35+7.42 (7×1H, t, d, d,t t, d, d, aromatic protons).

Melting Point: 167° C.

Mass: M+1 366 and 368 (Br-isomers) found.

D+E: Asenapine maleate

Process 1

In a 250 mL round-bottomed flask was trans-N-methyl-2-(2-hydroxyphenyl)-3-(2-bromo-5-chlorophenyl)-pyrrolidine (10.0 g, 27.3 mmol), cesium carbonate (11.0 g, 33.8 mmol), copper(I)chloride (1.0 grams, 10.10 mmol) and N,N-dimethylglycine (2.2 g, 21.33 mmol) in N,N-dimethylacetamide (22 ml) to give a brown suspension. The slurry was degassed with nitrogen and heated to 50° C. Toluene (88 ml) was added and the slurry was heated to 111° C. for 12-14 hours. When the reaction was complete (monitored by HPLC), the mixture cooled to 20° C. 90 ml of 3N ammonia was added and the mixture was stirred for 15 minutes. The aqueous layer was discarded. The organic layers were washed with 2×60 ml of 3N ammonia. The toluene layer was stirred for 30 minutes with ECOSORB GL-793 polymeric carbon (1.0 grams) and then filtered. The toluene was removed by vacuum distillation. 2-Propanol (10.0 ml) was added and vacuum distilled to remove the solvent and to leave asenapine as a yellowish oil. Maleic acid (3.5 g, 30.2 mmol) was dissolved in 2-propanol (55 ml) at 45-50° C. This solution was added to the yellow oil at 45-50° C. The solution was cooled to 10° C. over 3 hours and held at 10° C. for 2 hours. The solids were filtered and washed with 40 ml cold (0-5° C.) 2-propanol. The solids were dried at 40° C. to afford a white solid. Weight: 8.8 grams The asenapine maleate was recrystallized by dissolving the crude product in acetone (51.5 ml) at 55-60° C. and then slowly adding n-heptane (17.5 ml). Seed crystals were added and the mixture was stirred for an hour. Further n-heptane (43 ml) was added in the course of 1 hour while the temperature was maintained at 55-60° C. The mixture was stirred for an hour at this temperature and then cooled to 10° C. over 6 hours. After stirring for at least one hour at 10° C., the product was isolated by filtration and washed with of a 1:1 mixture of acetone and n-heptane (9 ml) which had been cooled to 5-15° C. The material was then dried in a vacuum oven at 60° C. Yield 8.8 g (88%) of asenapine maleate (orthorhombic crystal form). Purity according to HPLC 99.0%

$^1$H-NMR: (CDCl$_3$) 3.07 (3h, s, CH$_3$), 3.94 (6H, br s, pyrrolidine protons), 6.27 (2H, s, maleate protons), 7.00-7.26 (7H, m, aromatic protons).

Melting-point: 140-141° C.

Process 2

To a 250 mL flask, trans-N-methyl-2-(2-hydroxyphenyl)-3-(2-bromo-5-chlorophenyl)-pyrrolidine (5g, 13.6mmol), powdered Cs$_2$CO$_3$ (0.8 g, 2.5 mmol), powdered potassium carbonate (5.4 g, 29 mmol), CuCl (0.5 g, 5 mmol), N,N-dimethylglycine (1.1 g, 10.6 mmol) and N,N-dimethylacetamide (11 mL) were charged. The slurry is degassed with nitrogen and heated to 50° C. To the reaction mixture degassed toluene (44 mL) and water (1.5 mL) were added and then the resulting slurry was heated to 110-112° C. for 5-10 hours. The reaction is cooled to room temperature and 3 N aqueous ammonia (45 mL) was added and was stirred for 15 minutes. Separate the layer and wash the organic layer with 3 N aqueous ammonia (2×30 mL). The toluene is removed under vacuum to produce an oil. The salt is made in 2-propanol as described above.

Process 3

To a 500 mL flask were charged trans-N-methyl-2-(2-hydroxyphenyl)-3-(2-bromo-5-chlorophenyl)-pyrrolidine (10 g, 27.2 mmol), CuCl (1.0 g, 10.2 mmol), potassium carbonate (7.52 g, 54.4 mmol), N,N-dimethylglycine (2.2 g, 21.3 mmol) and 22 mL N,N-dimethylacetamide (22 ml). The slurry was degassed with nitrogen for 20 minutes and heated to 50° C. Degassed toluene (90 mL) was added followed by 2-methyltetrahydrofuran (10 mL). The mixture was heated to 110-115° C. for 4-5 hours with vigorous agitation. The reaction mixture was cooled to 20° C. Ammonium hydroxide (3N, 90 mL) was added. The mixture was filtered through celite. Methyl THF (20 mL) was added to the filtrate. The organic layer was washed two additional times with ammonium hydroxide (3N, 60 mL). Toluene was removed by vacuum distillation at 70-80° C. to give an oil. The salt is made in 2-propanol as described above.

Process 4

To a 500 mL flask were charged of trans-N-methyl-2-(2-hydroxyphenyl)-3-(2-bromo-5-chlorophenyl)-pyrrolidine (10 g, 27.3 mmol), CuCl (1.0 g, 10.1 mmol), potassium carbonate (7.52 g, 54.4 mmol), N,N-dimethylglycine (2.2 g, 21.3 mmol) and dimethylformamide (50 mL). The mixture was heated to 110-115° C. for 3-4 hours. The reaction was monitored by HPLC until the starting material was less than 2%. The reaction mixture was cooled to 20° C. Toluene (50 mL) was added followed by aqueous 3N NH$_4$OH (90 mL) and stirred for 20 minutes. The layers were separated. The aqueous layer was washed with toluene (3×50 mL). The combined organic layers were washed with 3N NH$_4$OH (3×60 mL). Toluene was removed by vacuum distillation at 70-80° C. to give an oil. The salt is made in 2-propanol as described above.

Example 4

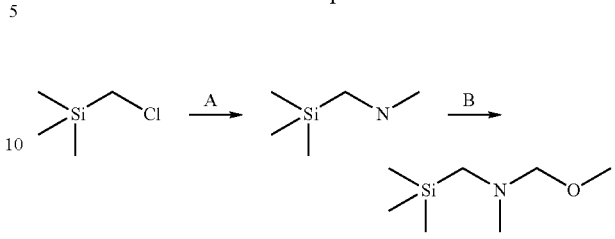

A: Methyl-trimethylsilanylmethyl-amine

A pressure flask (500 ml) was charged with chloromethyl-trimethylsilane (100 ml, 716 mmol) and 40% aqueous methylamine (373 ml, 4.29 mol). The reaction was heated to 85° C. for 6 hours, the reaction generates less than 690 mbar. The reaction was cooled to 20° C. and the layers were separated. The aqueous layer was cooled to 5° C. and solid potassium-hydroxyde (34 g, 0.607 mol) was added. The aqueous layer was washed with 1:1 pentane:t-butyl methyl ether (200 ml). The combined organics were concentrated in vacuo to about half volume. The product was distilled at 95-100° C.; yielding 38 grams (50%) of methyl-trimethylsilanylmethyl-amine (the product contains 10% mol/mol MTBE).

$^1$H-NMR: (CDCl$_3$) 0.00 (9H, s, Si(Me$_3$)), 0.61 (1H, s, NH), 1.99 (2H, s, CH$_2$), 2.42 (3H, 2, NMe).

Mass: M+1 118 found.

B: N-methoxymethyl-N-trimethylsilyl-N-methylamine

To a cooled solution (0° C.) of formaldehyde (37% in water, 8.5 grams) was added slowly a solution of methyl-trimethylsilanylmethyl-amine (205 g, 175 mmol) the temperature of the reaction mixture was below 5° C. Methanol (14 ml) was added, followed by potassium carbonate (12 g). After stirring for one hour the layers were separated. To the organic layer potassium carbonate (2 grams) was added and the organics were stirred for two hours. The potassium carbonate was removed by filtration and the product was distilled at 45° C. and 20 mbar.

$^1$H-NMR: (CDCl$_3$) 0.00 (9H, s, SiMe$_3$), 2.00 (2H, s, CH$_2$Si), 2.30 (3H, s, MeN), 3.25 (3H, s, OMe), 3.88 (2H, s, CH$_2$O).

Mass: M+1 162 found.

Example 5

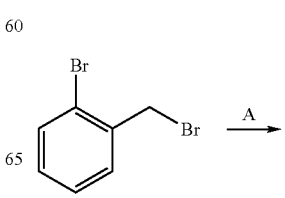

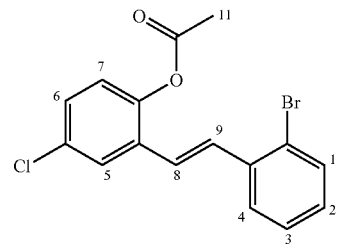

$^1$H-NMR (CDCl$_3$): 2.38 (3H, s, H-11); 6.87 (1H, d, H-9), 7.19+7.34 (2×1H, 2×t, H-2+H-3), 7.26 (1H, d, H-6), 7.46 (1H, d, H-8), 7.60 (2H, dd, H-1+H-4), 7.68 (1H, d, H-5).

C: trans-N-methyl-2-(2-bromophenyl)-3-(2-hydroxy-5-chlorophenyl)-pyrrolidine trans-2-Bromo-2'-acetoxy-5'-chlorostilbene (26 g, 73 mmol) was slurried in toluene (91 ml) at 33° C. Trifluoroacetic acid (200 microliters) was added. The N-methoxymethyl-N-trimethylsilyl-N-methylamine (14.5 g; 89.7 mmol) was added to the reaction mixture over 90 minutes. After addition, the reaction was washed with water (25 ml). The toluene was removed by vacuum distillation. Ethanol (30 ml) was added and removed under reduced pressure. The oil was dissolved in methanol (90 ml). Potassium hydroxide (5 grams in 25 ml water)) was added. The product began to precipitate immediately. After 30 minutes, the pH was adjusted to 8-9 with 3N HCl (8 ml). Added water (10 ml) and cooled to less than 10° C. Filtered and washed with 1:1 methanol: water. Dried in vacuum to 26.0 grams (96% yield). Purity according to HPLC is 98% a/a.

$^1$H-NMR (MeOD): 2.50 (3H, s, CH$_3$), 2.52+3.09+3.10+3.45 (4×1H, t, dd, t, t, Ha-5, Hb-5, Ha-6, Hb-6), 3.62+4.14 (2×1H, 2×m, H4 +H7), 6.72 (1H, d, H-1), 6.94 (1H, d, H-3), 6.98 (1H, d, H-2), 7.10+7.35 (2×1H, 2×t, H-10 +H-9), 7.52+7.58 (2×1H, 2×d, H-8+H-11).

D+E: Asenapine

See examples 1 or 3 step D+E

Example 6

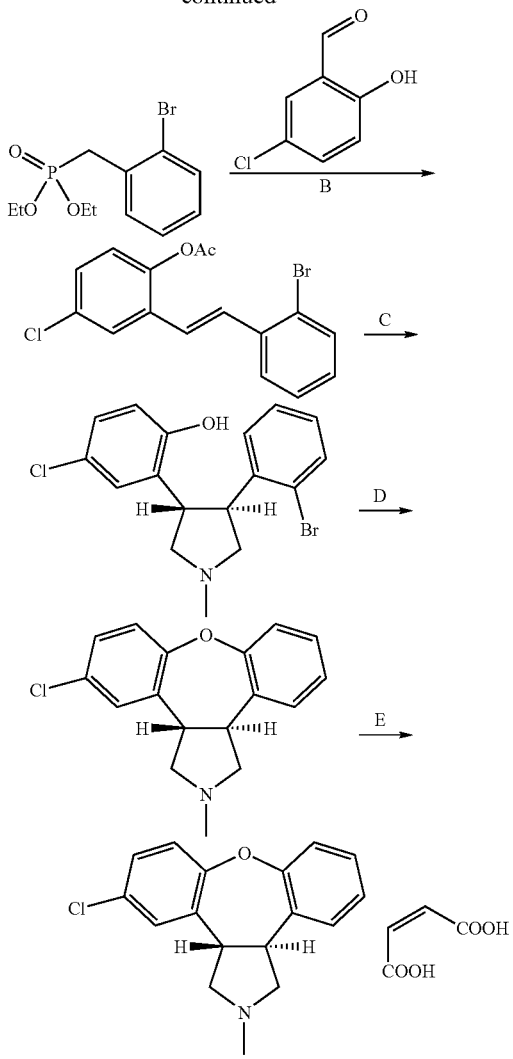

A+B: trans-2-bromo-2'-acetoxy-5'-chlorostilbene

2-Bromobenzyl bromide (25 g, 0.100 mol) and toluene (25 ml) were heated to 100° C. Next triethyl phosphite (19.3 ml, 0.108 mol) was added over 30 minutes, while the temperature was kept below 116° C. The mixture was stirred for 2 hours at 115° C., while the toluene was distilled. The mixture was cooled to room temperature and diluted with THF (37.5 ml). KOtBu (30.5 grams, 0.250 mol) was dissolved in THF (176 ml) and cooled to −10° C. The (2-bromo-benzyl)-phosphonic acid diethyl ester-solution was added at 5° C. Next chlorosalicylaldehyde (17.2 g, 0.110 mol) in THF (62 ml) was added at 5° C. The mixture was stirred for one hour at −5° C. to 0° C. When the reaction was complete acetic anhydride (28.3 ml, 0.301 mol) was added and the temperature was allowed to rise to 20° C. The reaction was complete in one hour and the mixture was cooled to 5° C. Next 250 ml 1N HCl is added rapidly. The organic layer is washed with 200 ml saturated NaCl solution. The organic layer is evaporated under reduced pressure at 50° C., yielding the title stilbene in 25.8 grams, (73%).

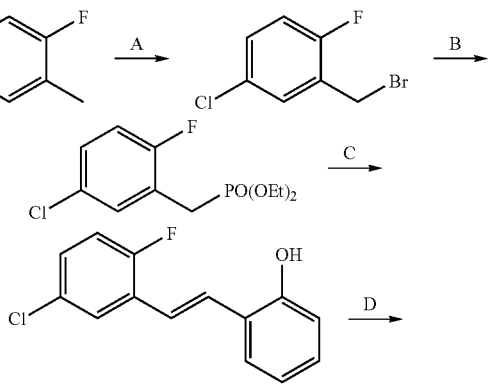

-continued

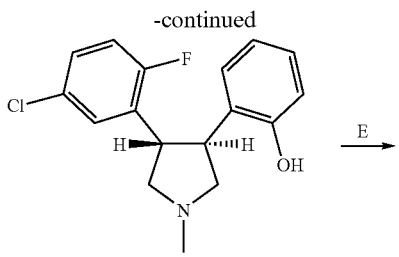

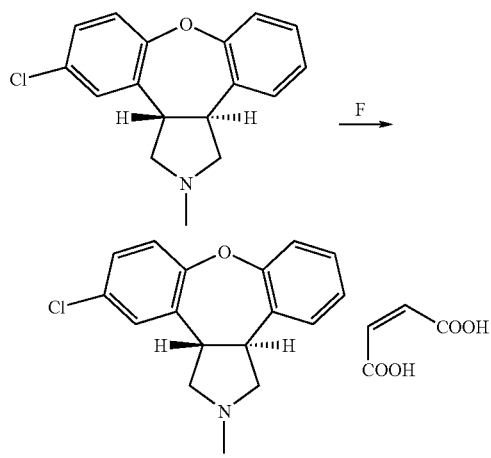

A: 5-chloro-2-fluoro-benzylbromide

5-Chloro-2-fluoro-toluene (100 g, 692 mmol) was dissolved in ethylactate (300 ml) at 20° C. To this solution N-bromosuccinimide (147.7 g, 830 mmol) and dibenzoyl peroxide (2 g, 8.25 mmol) was added. The mixture was stirred at 80° C. for 3 hours.

Heptane (300 ml) was added and the solution was cool to 0° C. whereupon succinimide precipitates. After filtration and washing with heptane, the residue was washed with water (1500 ml). The filtrate was concentrated in vacuo to dryness, yielding 162 grams of crude 5-chloro-2-fluoro-benzylbromide. Purification of the crude product (141 grams) was done by vacuum distillation at 99° C. and 33 mbar, this 5-chloro-2-fluoro-benzylbromide (99 grams, 75%). Purity according to GC is 87.1% a/a.

$^1$H-NMR (CDCl$_3$): 4.44 (2H, d, CH$_2$), 7.01 (1H, t, H3), 7.26 (1H, m, H4), 7.38 (1H, m, H6)

B: (5-chloro-2-fluoro-benzyl)-phosphonic acid diethyl ester

5-Chloro-2-fluoro-benzylbromide (630 g, purity according to GC 72% a/a, 2.42 mol) was heated at 100° C. and triethylphosphite (403 g, 2.42 mol) was added slowly in 1 h 45. The mixture was stirred for 2 hours at 100° C., and slowly THF (350 ml) was added and distilled off, until no ethylbromide was detected by NMR. To isolate the crude (5-chloro-2-fluoro-benzyl)-phosphonic acid diethyl ester the reaction mixture was cooled to room temperature, yielding 681 grams (100%).

C: trans-5-chloro-2-fluoro-2'-hydroxystilbene

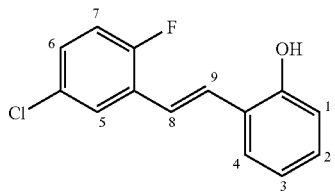

To a solution of potassium tert-butoxide (1088 g, 9.69 mol) in tetrahydrofuran (7 l) was added in 17 minutes at 0° C. crude (5-chloro-2-fluoro-benzyl)-phosphonic acid diethyl ester (680 g, 2.42 mmol) in tetrahydrofuran (3 l). To this reaction mixture a solution of salicylaldehyde (325 g, 2.66 mol) in tetrahydrofuran (3 l) was added over 1 hour. After stirring for 3 hours at 0° C. the reaction was complete. HCl (2M, 3 l) was added at 0° C. to obtain a acidic solution (pH=4.5). At 20° C. the organic phase was isolated, dried over magnesium sulphate, filtered and concentrated under reduced pressure. Coevaporation with heptane (2×700 ml) provides crude trans-5-chloro-2-fluoro-2'-hydroxystilbene, which is purified by adding MTBE (6.5 L) and NaOH (238 g) in 7.5 L. After stirring for 3.5 hours the organic layer was washed with HCl (1 M, 5 L) followed by saturated NaCl solution (4 L). Concentration under reduce pressure affords trans-5-chloro-2-fluoro-2'-hydroxystilbene (460 grams, 69%). Purity according to GC is 84% a/a.

$^1$H-NMR (CDCl$_3$): 6.79 (1H, dd, H1), 6.95 (1H, m, H3), 6.99 (1H, dd, H7), 7.15 (1H, m, H6), 7.17 (1H, m, H2), 7.21 (1H, d, H8), 7.44 (1H, d, H9), 7.54 (1H, dd, H4), 7.61 (1H, dd, H5)

Mass analysis: [M+C$_3$H$_5$]$^+$=289 and 291 [M+C$_2$H$_5$]$^+$=277 and 279, [M+H]$^+$=249 and 251, (Cl-isotopes found), and [MH−HCl]$^+$=213.

D: trans-N-methyl-2-(2-phenol)-3-(2-fluoro-5-chlorophenyl)-pryrolidine

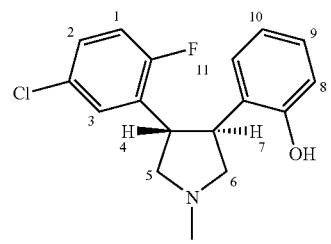

Process 1 using trimethylamine-N-oxide.dihydrate

To a solution of trans-5-chloro-2-fluoro-2'-hydroxystilbene (451 grams, 1.81 mol) in tetrahydrofuran (2.5 L) trimethylamine-N-oxide.dihydrate (272.9 g, 2.45 mol) was added at 5° C. Lithium diisopropylamide in cyclohexane (2M, 3.6 l, 3.62 mol) was then added during the course of 1 hour while maintaining the temperature at 5° C. After completion of the reaction saturated NH₄Cl (1.8 l) was added at −10° C. in 30 min. The organic solvent was evaporated and the obtained mixture, with a pH of 10 was extracted with ethyl acetate (2 l). Concentration under reduced pressure provides crude trans-N-methyl-2-(2-phenol)-3-(2-fluoro-5-chlorophenyl)-pryrolidine, which was dissolved in ethanol/water (855 mL, 3/7 v/v) at 80° C., slowly cooling was applied until 0° C. to recrystallize trans-N-methyl-2-(2-phenol)-3-(2-fluoro-5-chlorophenyl)-pyrrolidine. The crystals were isolated, and after drying under reduced pressure to gave the title pyrrolidine (207 grams, 40%). Purity according to GC 98.2% a/a.

¹H-NMR (CDCl₃): 2.44 (1H, m, H5), 2.54 (1H, s, CH₃), 2.90 (1H, t, H6), 3.19 (1H, d, H6), 3.33 (1H, m, H7), 3.56 (1H, m, H5), 3.61 (1H, m, H4), 6.65 (1H, m, H10), 6.79 (1H, dd, H11), 6.90 (1H, dd, H8), 6.98 (1H, m, H1), 7.12 (1H, m, H9), 7.17 (1H, dd, H3), 7.18 (1H, m, H2)

Process 2 using trimethylamine-N-oxide anhydrate

Trimethylamine-N-oxide anhydrate was prepared in-situ from trimethylamine-N-oxide dihydrate by coevaporation of water with toluene. To a solution of trans-5-chloro-2-fluoro-2'-hydroxystilbene (80 g, 320 mmol) in tetrahydrofuran (440 ml) trimethyl-amine-N-oxide anhydrate (48 g, 640 mmol) was added at 5° C. Lithium diisopropylamide in cyclohexane (1.5 M, 853 ml, 1.28 mol) was then added during the course of 5h30 hour while maintaining the temperature at 5° C. After completion of the reaction saturated NH₄Cl (320 ml) was added at −10° C. in 30 min. The organic solvent was evaporated and the obtained mixture, with a pH of 10 was extracted with ethyl acetate (355 ml). Concentration under reduced pressure provides crude trans-N-methyl-2-(2-phenol)-3-(2-fluoro-5-chlorophenyl)-pryrolidine, which was dissolved in ethanol/water (855 mL, 3/7 v/v) at 80° C., slowly cooling was applied until 0° C. to recrystallize trans-N-methyl-2-(2-phenol)-3-(2-fluoro-5-chlorophenyl)-pyrrolidine. The crystals were isolated, and after drying under reduced pressure to gave the title pyrrolidine (90.2 g, 92%). Purity according to GC 93.5% a/a.

¹H-NMR (CDCl₃): 2.44 (1H, m, H5), 2.53 (1H, s, CH3), 2.90 (1H, t, H6), 3.19 (1H, d, H6), 3.34 (1H, m, H7), 3.56 (1H, m, H5), 3.61 (1H, m, H4), 6.64 (1H, m, H10), 6.79 (1H, dd, H11), 6.90 (1H, dd, H8), 6.98 (1H, m, H1), 7.12 (1H, m, H9), 7.17 (1H, dd, H3), 7.18 (1H, m, H2)

Mass analysis: $[M+C_3H_5]^+$=346 and 348, $[M+C_2H_5]^+$=334 and 336, $[M+H]^+$=306 and 308 (Cl-isotopes found), E and F Asenapine maleate

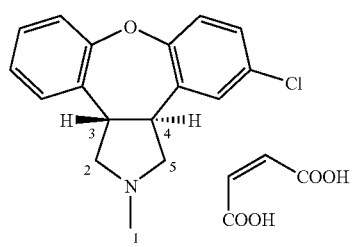

A mixture of trans-N-methyl-2-(2-phenol)-3-(2-fluoro-5-chlorophenyl)-pryrolidine (205 g; 0.67 mol) and potassium hydroxide (44 g; 0.78 mol) in N-methylpyrrolidone (2 l) was heated at 150° C. under nitrogen for 6 hours. After completion of the reaction the mixture was cooled 20° C. Water was added (7.2 l) to and extracted with ethyl acetate (2×3l). The organic layers were washed with water and saturated NaCl, concentrated under reduce pressure to afford crude asenapine in 187 grams yield. Purification was done by crystallisation as the HBr-salt: crude asenapine was dissolved in acetone (930 ml). Slowly 47% HBr in water (77 ml) was added. The suspension was heated to 36° C. to obtain a clear solution and after cooling, filtering and drying under vacuum at 50° C. asenapine bromide salt was isolated in 143 grams yield (58%). Purity according to GC is 94.8%. To obtain Org 5222, the bromide salt (134 grams, 0.36 mol) was neutralized with 28% aqueous solution of ammonia in water (700 ml). The free base was extracted with ethylacetate (2×500 ml) and the organic layer was washed with saturated NaCl. And concentrated under reduced pressure to yield 104 grams of asenapine, as the free base. The free base was dissolved in ethanol (208 ml) and heated to 60° C. Maleic acid (46.5 grams 0.40 mol) was added and the mixture was stirred for 2h at −15° C. whereupon the maleate precipitates. The crystals were collected by filtration, washed with ethanol (208 ml) and diisopropylether (208 ml). To obtain the desired polymorph the isolated crystals were dissolved in ethanol (180 ml) and water (20 ml) at 55° C. The temperature was reduced to 20° C. and the desired polymorph was precipitated slowly over 48 h. The crystals were filtered, wash with ethanol (100 ml) and dry under reduced pressure at 40° C. Yield 92 grams (36%). Purity according to HPLC 99.8% a/a.

¹H-NMR (MeOD): 3.14 (3H, s, CH₃), 3.79+4.08 (2×2H, 2×m, H2+H5), 3.93 (2H, m, H4+H7), 6.24 (2H, s, vinylic H's of maleic acid), 7.35-7.13 (7H, m, aromatic H's)

The invention claimed is:
1. A process for preparing asenapine of Formula I,

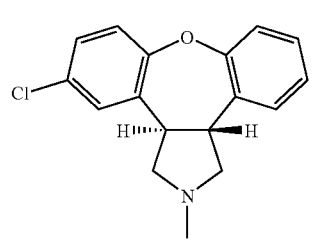

or a pharmaceutically acceptable salt thereof, characterised in that an E-stilbene derivative of Formula II,

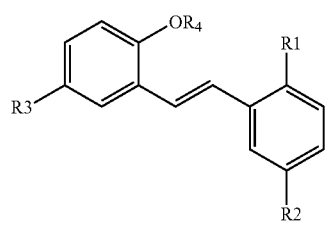

is reacted with an azomethine ylide to provide a trans-pyrrolidine derivative of Formula III,

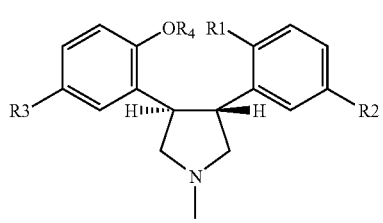

from which the protecting group, when present, is removed, and which is subsequently treated under conditions which effect an intramolecular ring-closure reaction to yield the compound of Formula I, and optionally converting the compound of Formula I to a pharmaceutically acceptable salt thereof, wherein $R_1$ is F, Br or I;

$R_2$ and $R_3$ are different and are each selected from H and Cl; and $R_4$ is H or a hydroxyl protecting group.

2. The process of claim 1 wherein $R_1$ is Br or I.

3. The process of claim 2 wherein $R_1$ is Br, $R_2$ is H, and $R_3$ is Cl.

4. The process of claim 1, wherein the azomethine ylide is generated in situ from trimethylamine-N-oxide or from N-methoxymethyl-N-trimethylsilyl-methyl-N-methylamine.

5. The process of claim 1, wherein the azomethine ylide is generated in situ from trimethylamine-N-oxide in combination with lithium di-isopropylamide or lithium tetramethylpiperidide.

6. The process of claim 1, wherein the azomethine ylide is generated from N-methoxymethyl-N-trimethylsilylmethyl-N-methylamine with the aid of trifluoroacetic acid.

7. A process for preparing the compound of Formula I,

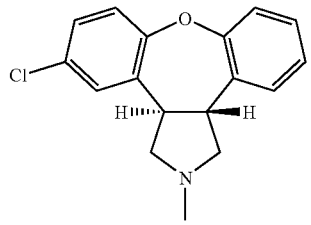

or a pharmaceutically acceptable salt thereof, wherein (E)-2-(2-bromostyryl)-4-chlorophenyl acetate,

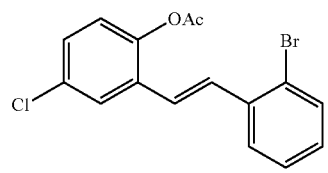

is reacted in an inert solvent with an azomethine ylide generated in situ from N-methoxymethyl-N-trimethylsilylmethyl-N-methylamine with the aid of trifluoroacetic acid to provide trans-N-methyl-2-bromophenyl-3-(2-acetoxy-5-chlorophenyl)-pyrrolidine,

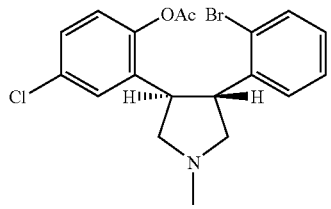

which pyrrolidine derivative is treated to remove the acetyl group, and which is subsequently treated under Ullmann conditions with the aid of a copper(I) salt to effect the intramolecular ring closure to give the compound of Formula I, and optionally converting the compound of Formula I to a pharmaceutically acceptable salt thereof.

* * * * *